United States Patent [19]

Kudo et al.

[11] Patent Number: 5,378,995

[45] Date of Patent: Jan. 3, 1995

[54] LOW MOLECULAR WEIGHT ORGANIC LIQUID DETECTION SENSOR IN THE SHAPE OF A WIRE AND DETECTOR USING THIS SENSOR

[75] Inventors: Toshio Kudo, Tokyo; Masaaki Nagai, Amagasaki; Yasuo Shiraiwa, Tokyo, all of Japan

[73] Assignee: Mitsubishi Cable Industries, Ltd., Amagashi, Japan

[21] Appl. No.: 25,135

[22] Filed: Mar. 2, 1993

[30] Foreign Application Priority Data

Mar. 5, 1992 [JP] Japan .................... 4-084450

[51] Int. Cl.⁵ .................... G01R 27/22; G01N 27/07; G01M 3/16
[52] U.S. Cl. .................... 324/693; 324/696; 324/698; 340/605; 200/61.04; 174/11 R; 73/40
[58] Field of Search ............... 324/555, 556, 693, 694, 324/696, 698; 340/603, 604, 605, 620; 200/61.04, 61.05, 61.08; 73/40, 40.5 R; 174/11 R

[56] References Cited

U.S. PATENT DOCUMENTS

| | | | |
|---|---|---|---|
| 3,295,088 | 12/1966 | Smith | 324/696 X |
| 4,082,997 | 4/1978 | Ohtsu et al. | 324/698 X |
| 4,862,066 | 8/1989 | Sato et al. | 324/696 |
| 4,918,977 | 4/1990 | Takahashi et al. | 73/40.5 R |
| 4,926,165 | 5/1990 | Lahlou et al. | 73/40 X |
| 5,173,684 | 12/1992 | Ijiri et al. | 340/605 |
| 5,177,996 | 1/1993 | Sahakian | 73/40 |

*Primary Examiner*—Gerard R. Strecker
*Assistant Examiner*—Diep Do
*Attorney, Agent, or Firm*—Varndell Legal Group

[57] ABSTRACT

A low molecular weight organic liquid detection sensor which is a wire body formed by coating a core material with a conductive layer made of a substantially non-crosslinked material having a Shore A hardness not more than 70 which is mainly composed of thermoplastic elastomer and conductive carbon, the conductive layer varying in its electric resistance upon contact with a low molecular weight organic liquid. The sensor of the invention permits secured mechanical strength, its easy installation in a narrow conduit or over a wide area, and highly sensitive sensing of a low molecular weight organic liquid in the longitudinal direction. The detector of the invention comprises a sensor having the above structure, preferably a porous body which houses and protects the sensor, a means which is connected to this sensor and detects electric resistance variation, and a means for transmitting this electric resistance variation as an alarm signal, and the detector can be used in the presence of underground water, which in turn permits use of existing liquid-leakage detection holes and installation at low costs.

19 Claims, 6 Drawing Sheets

LOW MOLECULAR WEIGHT ORGANIC LIQUID DETECTION SENSOR IN THE SHAPE OF A WIRE AND DETECTOR USING THIS SENSOR

FIELD OF THE INVENTION

This invention relates to a low molecular weight organic liquid detection sensor which is suitable for detecting a low molecular weight organic liquid such as gasoline or gas oil and a detector using this sensor.

BACKGROUND OF THE INVENTION

As one of the sensors for detecting a low molecular weight organic liquid like gasoline, there is such a sensor in which a conductive sheet prepared by dispersing a conductive carbon on a liquid-absorbing rubber sheet, etc. that swells upon absorption of liquid, is kept constantly conductive, and the sensor responds to an increased electric resistance attributable to the widened distance between carbon particles which is caused by swelling of the conductive sheet when it contacts gasoline, etc. The applicant of the present invention has proposed a highly sensitive liquid detection sheet-form sensor superior in swelling property as compared with conventional sensors upon contact with a liquid or its vapor to be sensed (U.S. Pat. No. 5,173,684).

The sheet-form sensor such as the above is useful when used as a liquid-leakage sensor installed in a place where liquid-leakage is predictable, that is, when used as a point type sensor. However, in cases where installation of many sensors to cover a wide area is required because of unpredictable points of liquid-leakage, that is, when area type sensing is necessary, there arises a problem of being unable to build an industrially practical detection system because of the likelihood of high cost for installing the above sheet-form sensors throughout the entirety of the target area.

It is desirable that a conductive layer for sensing a liquid should be formed into a thin layer to have high sensitivity. When the above sheet form sensor is formed into a thin layer, however, it is necessary to adhere a reinforcing sheet on one face of the layer to secure mechanical strength, and there also arises a problem of lowered detection sensitivity on the side of the reinforcing sheet.

Moreover, Japanese Utility Model Publication Jitsukou Sho 54-15672 (1979) describes use of a resistor wherein conductive powder is dispersed on epoxy resin, etc. as a sensing element for detecting oil leakage. Yet, the resistor made of such materials is disadvantageous in that it has poor processability such as extruding property, and a secondary processing for forming a desired shape is difficult.

At a gasoline station or the like, liquid leakage is detected by inserting a gaging bar into liquid-leakage detection holes having a diameter of about 30 mm which are provided on a periphery of an underground tank about once a week, and checking liquid-leakage by observing whether or not oil attaches on the bar. Or, in the case of a large-sized tank having a capacity of about 30 kl, the tank is formed into a double-structure, and liquid leakage is detected by filling ethylene glycol between the two tanks and checking change in liquid surface level by a measuring cylinder.

These methods have problems in that quick detection of leakage cannot be attained and that the tank becomes expensive.

SUMMARY OF THE INVENTION

It is an object of the present invention to provide a low molecular weight organic liquid detection wire-form sensor which is suitable for area type sensing and has high sensitivity, and furthermore, is easy to manufacture, especially a sensor suitable for detecting gasoline, gas oil, etc.

Another object of the invention is to provide a sensor capable of detecting water besides the above low molecular weight organic liquids mentioned above, with high sensitivity.

Still another object of the invention is to provide a low molecular weight organic liquid detector using the above wire-form sensor.

The above objects can be achieved by using a detection sensor which is a wire body formed by coating a core material with a conductive layer whose electric resistance varies upon contact with a low molecular weight organic liquid, the above conductive layer being made of a substantially non-crosslinked material having a Shore A hardness of not more than 70, which is mainly composed of thermoplastic elastomer and conductive carbon.

The low molecular weight organic liquid detector of the present invention comprises the above low molecular weight organic liquid detection wire sensor, a means which is electrically connected to said sensor and detects electric resistance variation, and a means for transmitting the detected electric resistance variation as an alarm signal, and said sensor is preferably housed in an electrical insulating porous body.

DETAILED DESCRIPTION OF THE INVENTION

According to the sensor of the invention, even when a trace amount of a low molecular weight organic liquid like gasoline or its vapor contacts the conductive layer, this layer swells and its electric resistance varies quickly. This variation in electric resistance can be detected by a measuring instrument, and thus, existence of low molecular weight organic liquid can be detected with high sensitivity.

Furthermore, the sensor being of a wire-form, sensing in the longitudinal direction thereof is possible.

Since the detector having the above structure comprises the wire-form sensor mentioned above, it is suitable for area type sensing and besides, insertion of the detector into an existing liquid-leakage detection hole, and so on is easily performed.

In addition, housing of the sensor in a porous structure results in precise detection, since the sensor is protected and unintended change in initial electric resistance of the conductive layer, caused by an external pressure, can be prevented.

Consequently, the sensor is suitable for the detection of leakage of gasoline, gas oil, etc. from an underground storage tank located in a gasoline station, a transport pipe such as an oil pipeline, or the like.

Figure 1:
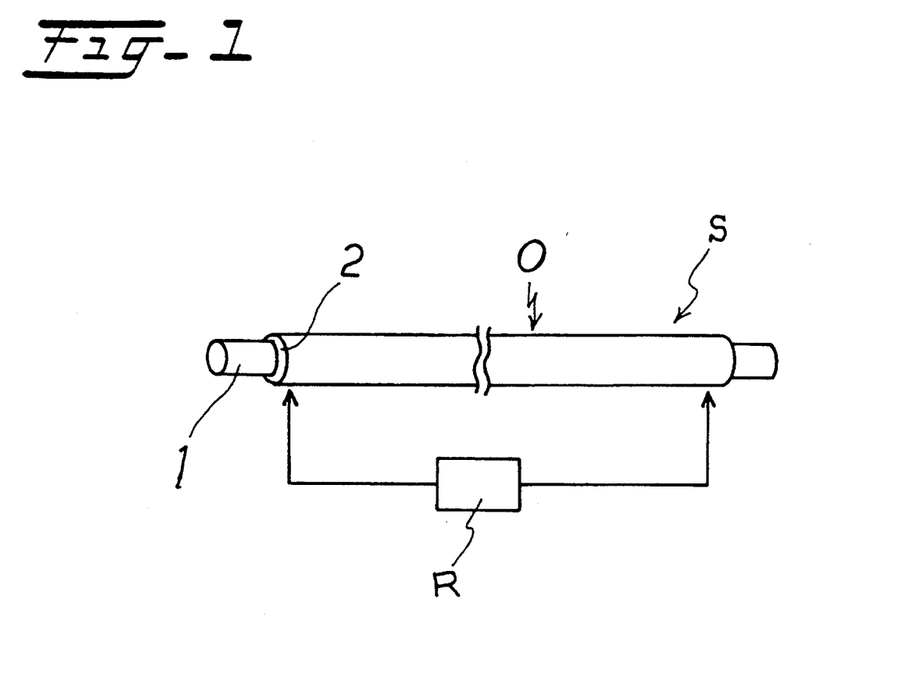
FIG. 1 is a side view showing a basic structure of the low molecular weight organic liquid detection sensor of the present invention.

FIG. 1 is a side view showing the basic structure of the low molecular weight organic liquid detection sensor of the present invention. In the figure, S is a low molecular weight organic liquid detection sensor, which is a wire body formed by coating a core material 1 with a conductive layer 2 which is made of a material mainly composed of thermoplastic elastomer and conductive carbon, and having a Shore A hardness of not more than 70 and a substantially non-crosslinked structure. In this sensor S, a pair of terminals extending from a measuring instrument R which has functions of electric current conduction and electric resistance measurement, are connected to the respective ends of the conductive layer 2. Existence of organic liquid like gasoline can be detected according to the variation in electric resistance of the conductive layer 2, which appears when organic liquid like gasoline or its vapor O contacts the layer 2.

The thermoplastic elastomer to be used for the conductive layer of the sensor above is not limited to a specific material and, for example, styrene.ethylene.-butadiene.styrene copolymer (SEBS), styrene.-butadiene.styrene copolymer (SBS), butadiene elastomer, or olefin elastomer may be used.

Also, the conductive carbon is subject to no limitation, and conductive carbon black such as KETZEN BLACK by Lion Co. Ltd., Japan, furnace black such as VULCAN XC-72 by Cabot Inc., U.S.A., acetylene black such as DENKA Acetylene Black by Denki Kagaku Kogyo K.K., Japan, or the like, having a minimum DBP oil absorption of 250 ml/100 g, and a minimum surface area of 500 m$^2$/g is especially preferable.

The ratio of the above-mentioned thermoplastic elastomer and conductive carbon is 10–100% by weight, preferably 12–90% by weight, especially preferably 15–80% by weight of the carbon relative to 100% by weight of the elastomer.

Preferably, the blend of thermoplastic elastomer and conductive carbon which constitutes the conductive layer is substantially non-crosslinked and has a Shore A hardness (hardness of rubber) of not more than 70, preferably not more than 65, especially preferably about 50 from the aspect of swelling by liquid absorption and processability. The conductive layer having a Shore A hardness exceeding 70 is disadvantageous in that the layer scarcely exhibits swelling by liquid absorption upon contact with a low molecular weight organic liquid, which in turn results in unclear variation in the electric resistance of the conductive layer and poor sensor function, and that the layer is so hard as to make its processability poor.

In the present invention, "substantially non-crosslinked" means that the thermoplastic elastomer to be used includes those partially crosslinked to the degree that thermoplasticity is maintained. That is, the non-crosslinked thermoplastic elastomer in the present invention includes not only perfectly non-crosslinked polymers which underwent no crosslinking process before and after the formation of a conductive layer, but also polymers partially crosslinked before processing into the layer. The degree of crosslinking when the polymer is partially crosslinked, according to JIS C3005 and expressed by gel percentage measured at 50° C. extraction temperature against xylene, is 3–50%, preferably 4–40%, more preferably 5–30%.

It is preferable to add a suitable amount of an oil-absorbing swelling agent to the conductive layer material in order to improve swelling property. Addition of an oil-absorbing swelling agent can result in greater degree of swelling of the conductive layer upon contact with the liquid to be detected, and variation in the electric resistance becomes greater even when only a trace amount of an organic liquid or its vapor exists, thus permitting higher sensitivity of the sensor.

The above core material 1 mainly plays the role of a mechanical reinforcement of the conductive layer 2. That is, the conductive layer which has been made thinner to seek higher sensitivity requires a core material so as to mechanically reinforce the layer.

The core material is not subject to any limitation, and an insulating rubber or plastic rod is suitable for facilitating detection of the resistance variation of the conductive layer. Other than these, a metal rod provided with an insulation costing, a conductor core made by coating a conductor to be mentioned later with rubber or plastic, or the like can be preferably used.

As a means for forming a conductive layer on a core material, there are methods including axially wrapping or longitudinally wrapping a conductive tape around the core material. A method of extrusion coating of a molten conductive layer material on a core material is the simplest and most desirable method. The conductive layer material in the present invention has an advantage of good processability during extrusion coating.

Low molecular weight organic liquids to be detected by the sensor of the present invention are organic liquids preferably having a molecular weight of not more than 300, especially not more than 150 and include, for example, alcohols such as methanol and ethanol; lubricating oils such as transformer oil; ketones such as methyl ethyl ketone and acetone; gas oil; kerosene; gasoline; naphtha; ligroin; benzene; toluene; xylene; and chlorine solvents such as chloroform. These organic liquids usually have a liquid form at room temperature.

When the low molecular weight organic liquid detection wire-form sensor of the present invention is actually used, it is desirable to attach, on the respective ends of the wire-form sensor, electrodes for measuring electric resistance.

As the electrodes, ring-form electrodes of aluminum, copper, or the like can be used and they can be attached to the sensor by crimping. In the example shown in FIG. 2, electrodes 3 and 3' are respectively attached to each end of the conductive layer 2, and connected to lead wires 31 and 32 extending from a measuring instrument R. The measuring instrument R desirably has an intrinsically safe structure.

Figure 2:
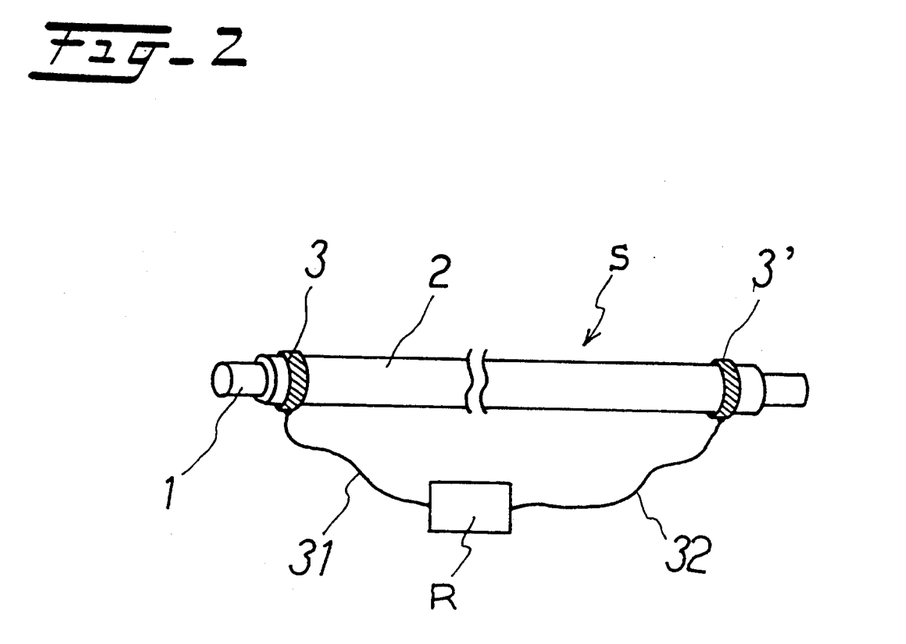
FIG. 2 is a side view showing an arrangement for connecting an electric resistance measuring instrument to a low molecular weight organic liquid detection sensor.

In the above arrangement, it is desirable to set the electric resistance between the electrodes 3 and 3' before contact with a low molecular weight organic liquid, i.e. initial electric resistance, to not more than 500 kΩ, preferably not more than 100 kΩ. A high impedance exceeding 500 kΩ for the initial electric resistance is undesirable, since the sensor becomes susceptible to an externally-induced noise, which can cause inability to correctly detect variation in electric resistance upon contact with a low molecular weight organic liquid.

The electric resistance between electrodes can be adjusted by selecting the length of the wire-form sensor, that is, the length of the conductive layer such that its resistance becomes not more than a predetermined value, or by adjusting the space between the electrodes, or by varying the carbon amount in or the thickness of the conductive layer.

Figure 3:
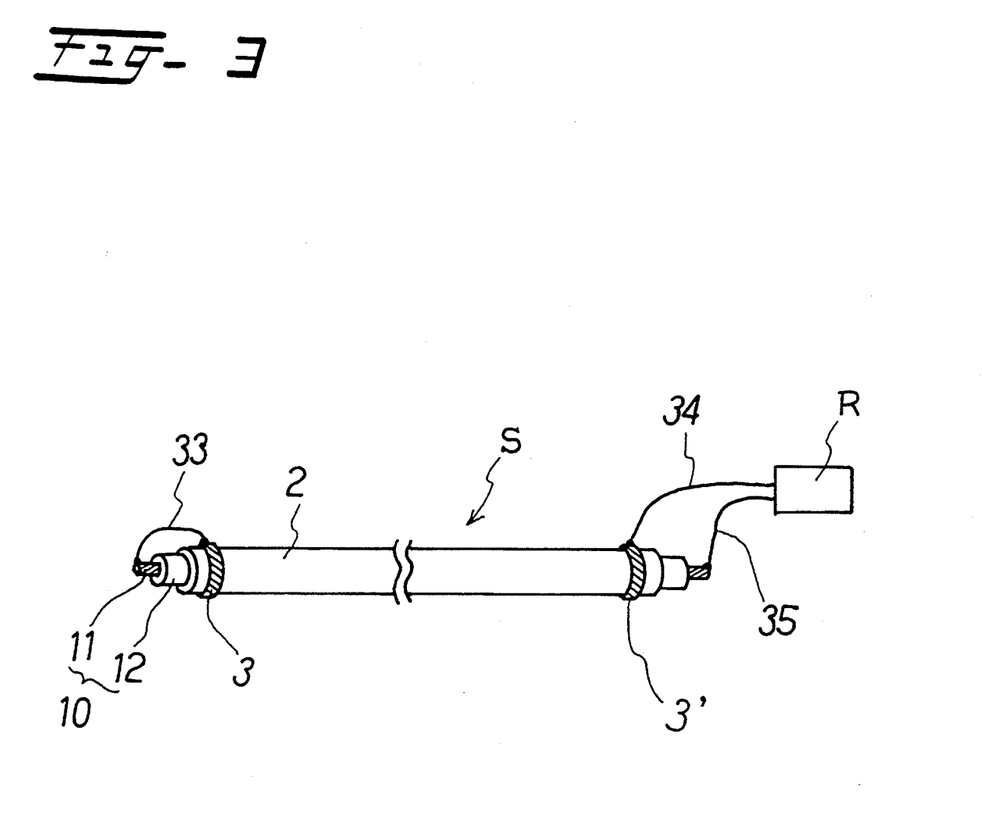
FIG. 3 is a side view showing the structure of a sensor using a conductor core formed by providing an electrical insulating layer on a conductor.

As the core material, use of a conductive core formed by coating a conductor with an insulating material is one of the preferable embodiments of the present invention. FIG. 3 shows such an example, in which a conductor 11 and an electrode 3 are connected by a lead wire 33 at one end of the sensor S, and an electrode 3' at the other end and the conductor 11 are connected to the measuring instrument R by lead wires 34 and 35.

When using a conductor core in such a way as mentioned above, one end of the conductor can be used in place of the lead wire of the electrode add one end of the sensor can serve as a measuring terminal.

In this way, the terminals for measuring the electric resistance are located Dear to each other, by which connection with the measuring instrument is facilitated and furthermore, suspension of the sensor in the vertical direction and formation of a long-sized wire-form sensor are made feasible.

Figure 4:
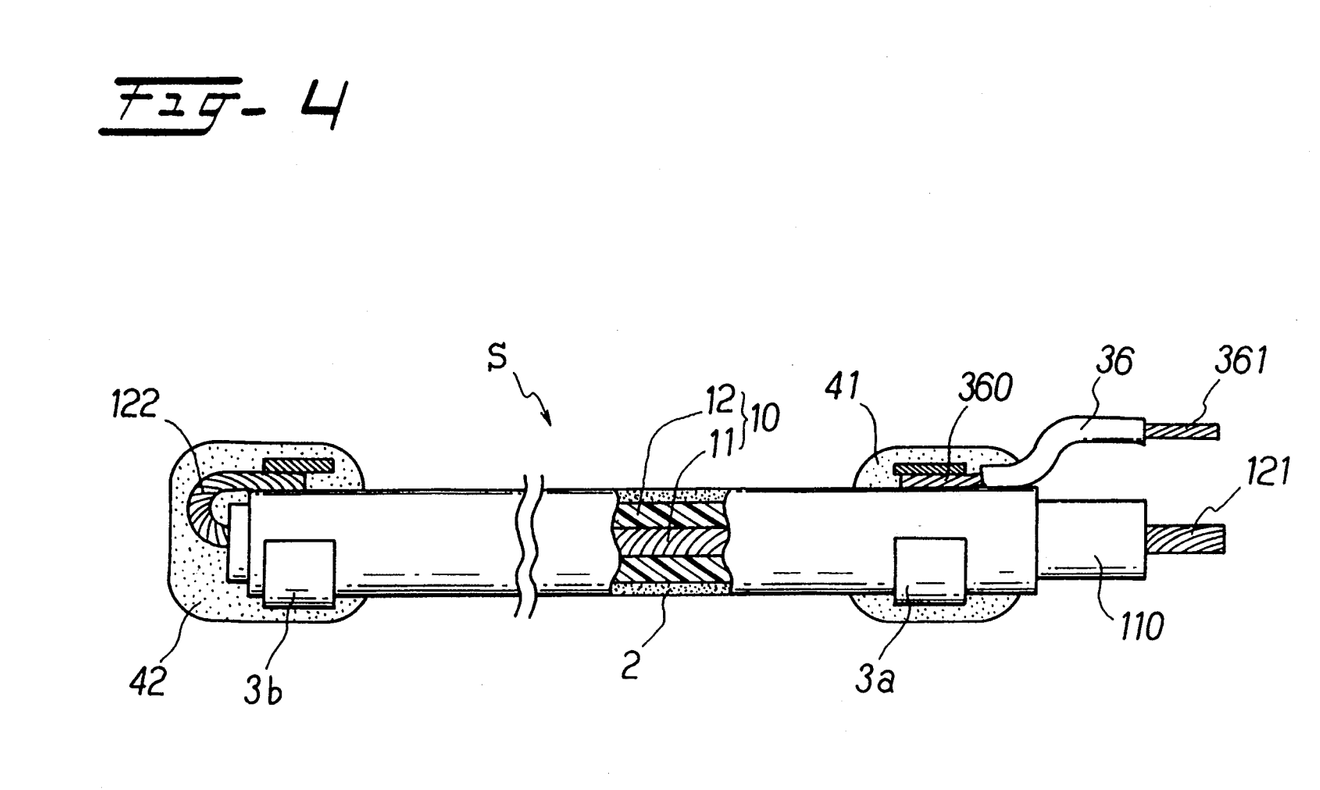
FIG. 4 is a partially broken side view showing one embodiment of the low molecular weight organic liquid detection sensor of the present invention.

FIG. 4 is a partially broken view showing a more concrete embodiment of the sensor of the present invention. In this figure, S is a sensor, in which a conductor core 10 is formed by providing a conductor 11 with an insulation coating 12, and the conductor core 10 is coated with a conductive layer 2. At one end of this sensor S, a conductor 122 extending from the conductor core 10 is connected to the upper surface of the conductive layer 2 by crimping, using a ring-form electrode 3b. At the other end of the sensor S, a conductor 360 of a lead wire 36 is connected to the upper surface of the conductive layer 2 by crimping, using a ring-form electrode 3a, and a conductor 121 of the conductor core and a conductor 361 of the lead wire 36 are used as terminals for measuring electric resistance.

Preferably, the material of the insulation coating to be applied to the above conductor core is fluororesin such as ethylene-tetrafluoroethylene (ETFE) or polytetrafluoroethylene (PTFE), which does not swell upon contact with a low molecular weight organic liquid so that it may not have a bad effect on swell-deformation of the conductive layer.

Also, watertight insulation coatings 41 and 42 formed on the electrical connections of the above ring-form electrodes 3a and 3b, by using epoxy resin, water-proof shrinkage tubes, or the like are preferable, since galvanic corrosion at the ring-form electrodes 3a and 3b can be retarded, and the sensor function is not impaired even when the sensor is in contact with water.

The sensor function of the sensor S of the above structure is not impaired even when the sensor is in contact with water, since the electrical connections are provided with a watertight insulation coating, and for example, the sensor can function even in the presence of underground water to satisfactorily detect a trace amount of a low molecular weight organic liquid existing in the state of a thin layer on a water surface.

The above sensor S can be used as it is, but housing the sensor in an electrical insulating porous body is preferable so as to prevent any change in the initial electric resistance of the sensor which may be caused by an external force applied during transportation or installation of the sensor.

This porous body is formed into, for example, a cylinder by molding, laminating or braiding, using a material such as rigid polyvinyl chloride, nylon, polypropylene, polyester, or fluororesin such that the porous body can house the sensor in close contact with the surface of the above wire-form sensor, or with a space.

In the present invention, it is preferable that the above electrical insulating porous body should be formed, on the sensor's outermost layer, into a cylindrically braided body made of fiber yarns by using, for example, polyester or fluororesin fibers of about 200 denier.

The above cylindrically braided body may be either a tight fitting or a loose fitting. In consideration of swelling and deformation of the conductive layer 2, however, a loose fitting is preferable.

Figure 5:
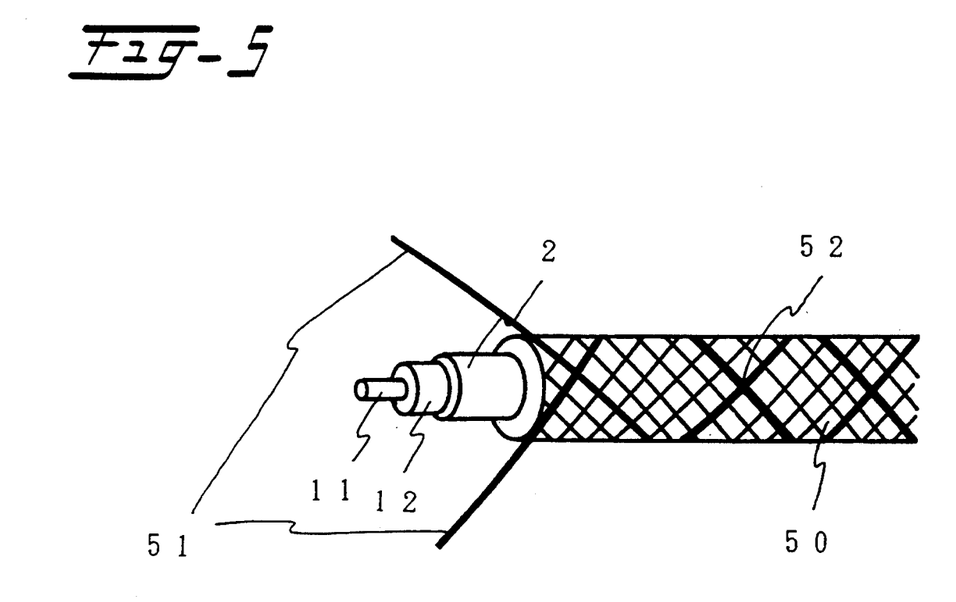
FIG. 5 is a perspective view showing the structure of a sensor provided, on its outermost layer, with a protective layer made of an electrical insulating porous body having a water detection function.

Imparting a water detection function to the above-mentioned braided body is one of the preferable embodiments. As shown in FIG. 5, this braided body 50 is so formed that at least one yarn from each of the weft group and the warp group making the braid on the conductive layer 2, are water detection wires 51 of copper wires coated with, for example, water soluble polymer, water absorbable polymer, or water swelling polymer, and the conduction state between both detection wires 51 and 51 is monitored by a measuring instrument.

When water attaches on the braided body, the above varnish layer of the water detection wire mentioned above melts, and short-circuit or deterioration of insulation resistance occurs at a cross point 52 of the detection wires, which can be confirmed by a measuring instrument.

Figure 6:
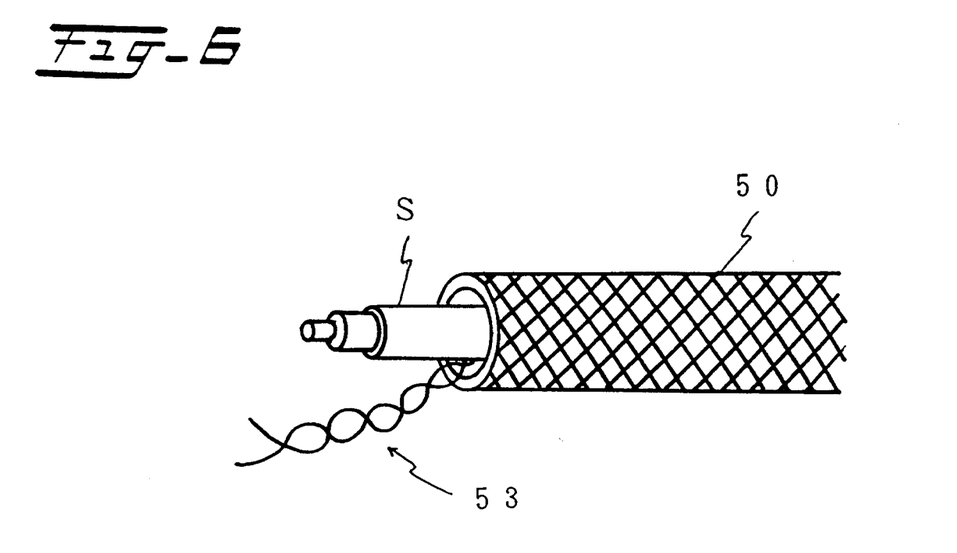
FIG. 6 is a perspective view showing another structure of a sensor provided, on its outermost layer, with a protective layer made of an electrical insulating porous body having a water detection function.

As shown in FIG. 6, a paired strand wires 53 may be interposed between the sensor S and a braided body 50.

Figure 7:
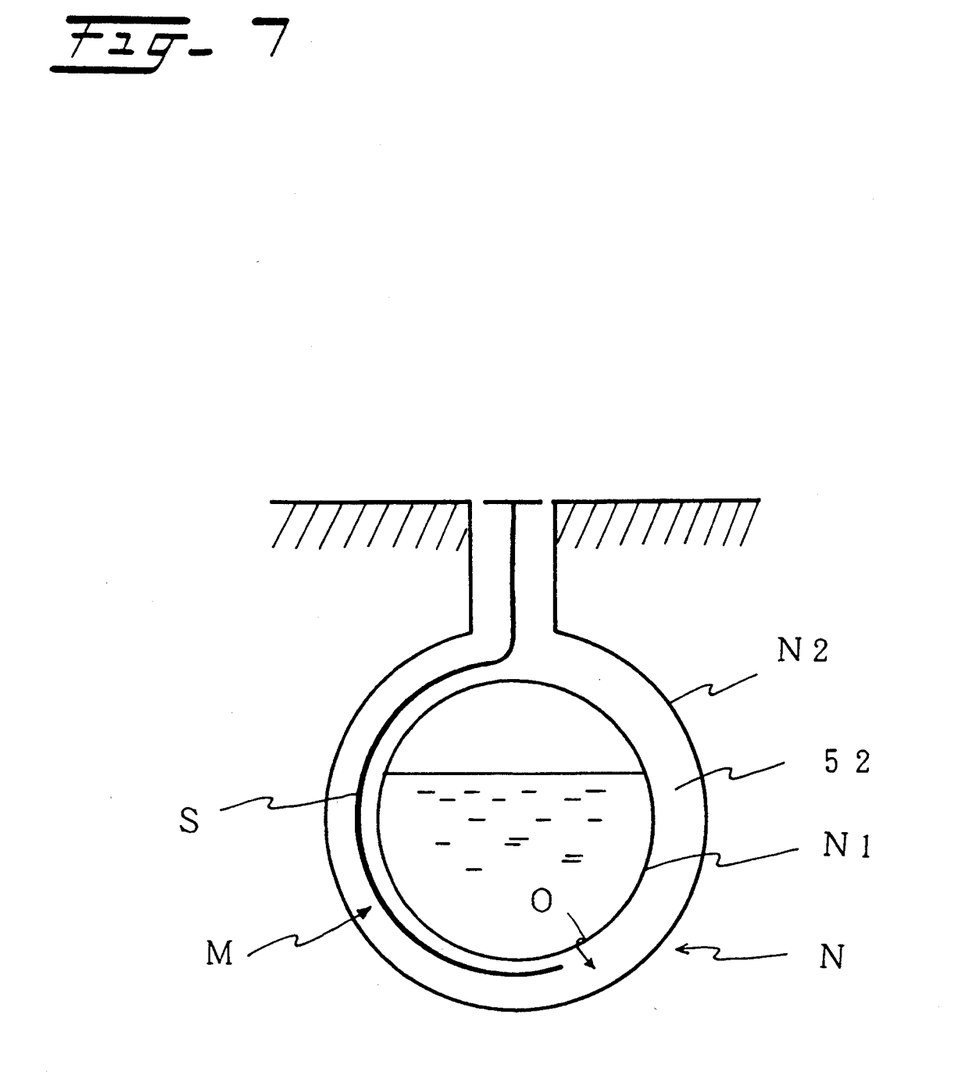
FIG. 7 is a sectional view showing an application example of a sensor provided, on its outermost layer, with a protective layer made of an electrical insulating porous body having a water detection function.

The sensor S imparted with the water detection function as described is suitable for use as a sensor to be installed in a clearance 52 between an inside tank N1 and an outside tank N2 of an oil tank N having a double wall structure as shown in FIG. 7.

That is, the sensor can detect leakage of organic liquid 0 caused by the damage of tank N1, as well as intrusion of underground water M caused by the damage of the outside tank N2, thereby enabling to detect any damage of both the inside tank N1 and the outside tank N2 with the use of one sensor.

Figure 8:
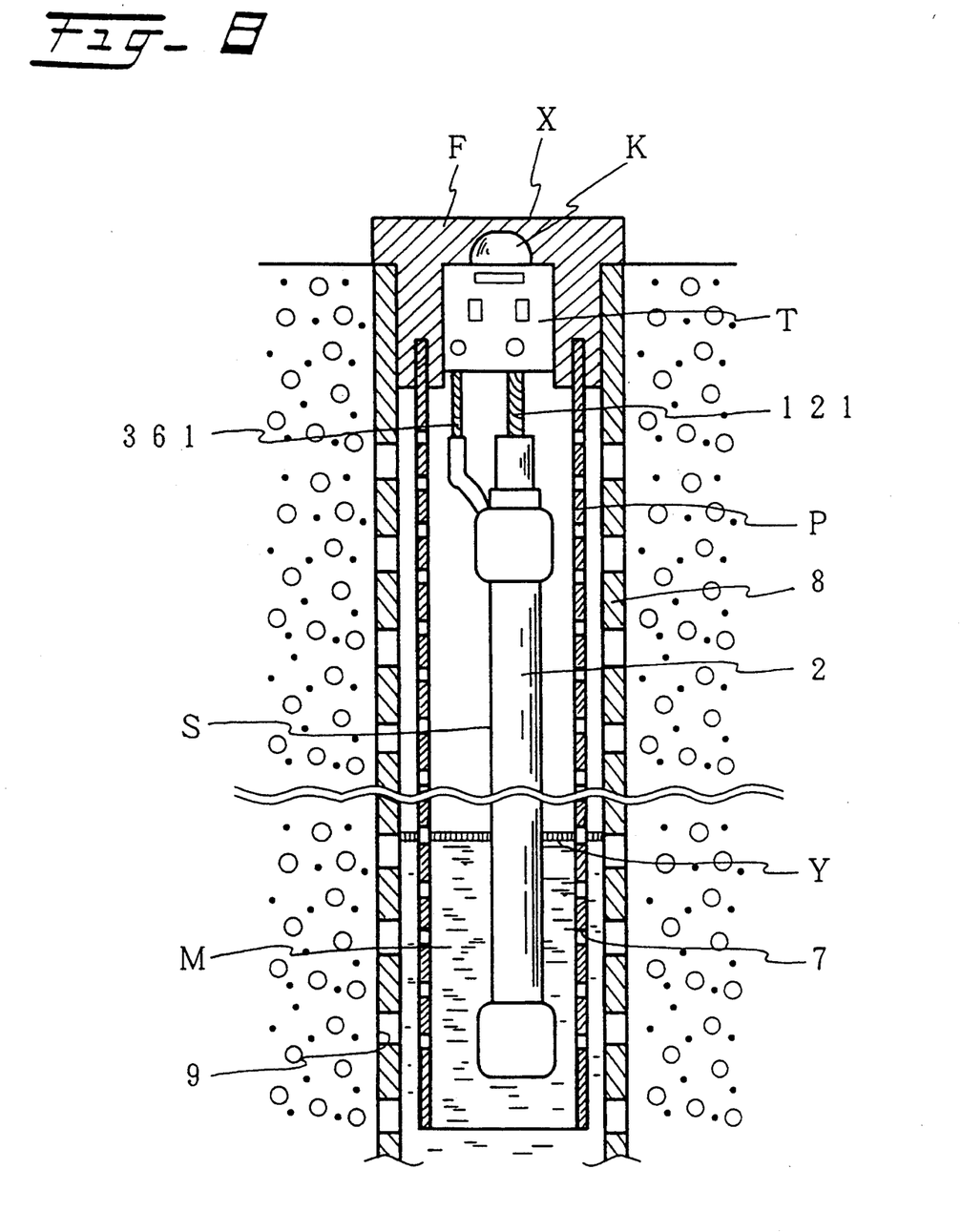
FIG. 8 is a side view showing one embodiment of the low molecular weight organic liquid detector of the invention.

FIG. 8 is a partial sectional view showing one embodiment of the detector using the low molecular weight organic liquid detection sensor of a wire form having the above structure, and an application example of the embodiment, In the figure, X is a detector which is installed in a liquid-leakage detection hole 9 provided on a periphery of an underground gasoline tank. The detector X comprises the low molecular weight organic liquid detection sensor S of a wire form, an electrical insulating porous body P for housing this sensor, a means T for detecting variation in electric resistance, which is electrically connected to the above sensor S, a means K for transmitting detected resistance variation as an alarm signal, and a cap body F mounted on the top of the above porous body P. In this example, the alarm signal transmitting means K to be connected electrically, and the electric resistance variation detection means T are internally contained in the cap body F.

As the above sensor S, one shown in FIG. 4 is used.

The electric resistance variation detection means T is connected to a terminal of the sensor S, and upon running a microcurrent flow in this circuit, detects current variation caused by the increase in the resistance of the conductive layer of the sensor S.

With respect to the alarm signal transmitting means K, any type may be used so long as it can be electrically connected to the above electric resistance variation detection means T, and so long as it can convert electric resistance variation detected by this means T into some form of an alarm signal such as light, sound, radio signals, or the like. Examples thereof include a light emitting device using an LED, an alarm signal device, and a radio signal transmitting device utilizing a weak radio wave.

Since the detector having the above structure comprises a wire-form sensor, it is suitable for use as an area type sensor capable of sensing in the longitudinal direction, and can be inserted easily into existing liquid-leakage detection holes.

Moreover, the sensor function of the detector is not impaired even when it is in contact with water, which in turn means that the sensor can be used to detect a low molecular weight organic liquid even in the presence of underground water in liquid-leakage detection hole.

Accordingly, existing liquid-leakage detection holes can be also used for this purpose, irrespective or presence of absence of underground water in the holes, and the sensor can surely detect a low molecular weight organic liquid even when underground water has intruded in the liquid-leakage detection holes.

In addition, since the sensor is housed in a porous structure, the sensor is protected and is free of unintended change in the initial electric resistance of the conductive layer which can be caused by an external pressure, with the result that a precise detection can be achieved.

Furthermore, since an alarm signal is transmitted when the sensor detects a low molecular weight organic liquid, existence of a low molecular weight organic liquid can be easily recognised.

Operation of the above detector in an application example of FIG. 8 is explained in the following.

When a low molecular weight organic liquid such as gasoline or gas oil leaks from an underground tank, this liquid intrudes into a liquid-leakage detection hole, pools on the bottom, and generates vapor. If underground water has intruded in the detection hole, the low molecular weight organic liquid which is lighter than water forms a thin layer on the water surface.

FIG. 8 shows the state when underground water M has intruded in a hole. In this situation, the electric resistance of the conductive layer 2 quickly varies upon contact of the thin layer of the low molecular weight organic liquid Y with the conductive layer 2 of the sensor S, and this variation is detected by the electric resistance variation detector T, after which the electric resistance variation thus detected is converted into an alarm signal by the alarm signal transmitting means K connected to the detector T to transmit the alarm.

As explained in the above, since the low molecular weight organic liquid detection sensor of the present invention is formed into a wire form and has a conductive layer made of a specific material, it permits detection of a trace amount of a low molecular weight organic liquid, and easy installation in a narrow conduit or installation for the detection covering a wide area. Alternatively, the sensor of the invention is extremely suitable for use as an area type sensor.

The structure of the sensor wherein a wire-form core material is coated with a conductive layer permits sensing of an organic liquid in the longitudinal direction and securing of mechanical strength of the sensor as well, even when the conductive layer is made thin for high sensitivity. In addition, the conductive layer made of the material used in the present invention is superior in processability such as extruding property, and the sensor can be easily manufactured.

In the sensor provided with an electrical insulating porous body on the outermost layer to impart mechanical strength to the sensor, the sensor is protected such that a change in the initial electric resistance caused by an external pressure can be prevented, thus resulting in the precise sensor function of the sensor.

In addition, the low molecular weight organic liquid detector of the present invention uses a wire-form sensor and can cope with increasing underground water level, with the result that liquid-leakage detection holes usually installed at a gasoline station, etc. can be used as they are for the detection, and installation of the detector can be easily performed, making the installation cost low.

Therefore, the detector is suitable for use in a place where liquid-leakage of low molecular weight organic liquid such as gasoline or gas oil from an underground storage tank or a transport pipe such as an oil pipeline is to be detected over a wide area.

The present invention is detailedly explained in the following by illustrating the embodiment of the invention.

As shown in FIG. 4, a conductor core 10 having an outer diameter of 0.6 mm was formed by providing an ethylene-tetrafluoro-ethylene coating 12 on an annealed copper wire 11, and a wire-form sensor S having a length of 2 m was produced by coating the conductor core 10 with a conductive layer 2 having a thickness of 250 μm. The conductive layer 2 was formed with a material having a Shore A hardness of 52 which was made by mixing 100 parts by weight of a thermoplastic elastomer, SEBS, and 25 parts by weight of a conductive carbon, KETZEN BLACK (Lion Co., Ltd., Japan).

At one end of the sensor S, a conductor 360 of a lead wire 36 was crimped on the upper surface of the conductive layer 2 with a ring-form electrode 3a, on which a watertight insulation coating 41 was formed with epoxy resin. At the other end of the sensor S, a conductor 122 extending from the conductor core 10 was folded back up on the upper surface of the conductive layer 2 and crimped on that surface with a ring-form electrode 3b, on which a watertight insulation coating 42 was formed in the same manner as above. An end conductor 361 extending from the above lead wire 36 and a conductor 121 extending from a conductor core 110 were used as the terminals for electric resistance measurement.

Having connected these terminals 361 and 121 to a tester (not shown), the initial electric resistance of the sensor S was measured and found to be 80 kΩ.

In order to verify the operation of the wire-form sensor S fabricated as above, a thin gasoline layer having a thickness of about 1 mm was formed on water in a beaker, through which the sensor S was partially placed in water up to 50 cm from the bottom end. Then, the terminals 361 and 121 on the upper end of the sensor were connected to the electrodes of the tester R to measure variation in the electric resistance.

This wire-form sensor S was provided with the watertight insulation coatings 41 and 42 as mentioned above, and thus, even when the bottom end thereof was in water, the function of the sensor was not impaired, and the variation in the electric resistance could be measured. The measurement result was that the electric resistance started to rise at 30 seconds from the partial soaking of the sensor S and it reached 120 kΩ in 1 minute, 400 kΩ in 2 minutes and 2.4 MΩ in 3 minutes, by which it was verified that the sensor had a superior gasoline detection function.

A sensor same as the above was partially placed in water in a beaker (up to 50 cm from the bottom end), on which a thin gas oil layer having a thickness of about 1 mm had been formed in place of the gasoline, and the variation in the electric resistance was measured by the tester R in the same way as above. As a result, it was found that the electric resistance rose to 90 kΩ in 5 minutes from the partial soaking, to 110 kΩ in 10 minutes, to 560 kΩ in 15 minutes and to 1 MΩ in 20 minutes, by which it was verified that the sensor had a practically satisfactory function, though somewhat inferior in quick response as compared with the case of gasoline.

A detector shown in FIG. 8 was produced using the wire-form sensor S of the above embodiment. In the figure, X is a detector, in which terminals 361 and 121 of the wire-form sensor S are connected to an electric resistance variation detector T housed in a cap body F, and this detector T is connected to an LED lamp K. The sensor S is housed in a cylindrical, porous pipe P made of polyvinyl chloride and having a number of pores 7 on its side face. On the top of this porous pipe P, the cap body F made of transparent resin is mounted.

The detector X having the above structure was inserted into a liquid-leakage detection hole 9 of a diameter of about 30 mm and a depth of about 2.5 m, which had been installed on a periphery of an underground tank of a gasoline station. On the inner periphery of this liquid-leakage detection hole 9, a cylindrical, porous pipe 8 of an outer diameter of about 26 mm and a length of about 2.5 m made of polyvinyl chloride and having a number of pores on its side face was previously inserted.

When gasoline Y leaked from the underground tank (not shown), the gasoline intruded into the liquid-leakage detection hole 9 through the pores of the porous pipe 8. If underground water M intrudes into the liquid-leakage detection hole 9 at this point, the gasoline Y would form a thin film on the surface of the underground water M. When the gasoline Y contacted the conductive layer 2 of the sensor S, the electric resistance of the conductive layer 2 varied and this electric resistance variation was detected by the above detector T, and then the detected signal was transmitted to the LED lamp K to light the LED lamp K, and an alarm signal indicating gasoline leakage was transmitted.

In this way, the detector of the present invention, when having a structure in which a wire-form sensor is assembled in a porous pipe, is advantageous in that insertion of the sensor into such a narrow hole is easy, and that the sensor immediately detects gasoline or the like upon contact.

Even if underground water intrudes into a liquid-leakage detection hole, the sensor is able to quickly detect gasoline or the like on the water surface upon contact. Thus, existing liquid-leakage detection holes conventionally installed on a periphery of an underground gasoline tank, into which underground water could intrude, can be utilized without modification.

While the explanation has been focused on the case of an underground gasoline tank in the above embodiment, the detector of the invention is also useful for the detection of liquid-leakage from a metal transport pipe such as an oil pipeline. In this case, the sensor of the invention may be installed along with the metal pipe in its longitudinal direction or wound around the metal pipe. In such manners of use, however, correct detection of the electric resistance variation may be occasionally prevented by a short-circuit between the metal pipe and the conductive layer of the sensor. So as to secure precise detection, it is desirable that a spacer layer for preventing short-circuit be provided by, for example, forming an insulation braid coating or an insulation porous coating on the conductive layer, or installing insulation rings at predetermined intervals.

As the spacer material, a water repellent material is preferably used so that its contact with an organic liquid to be detected will not be prevented by a membrane of water, etc. formed on the spacer material.

What is claimed is:

1. A low molecular weight organic liquid detection sensor comprising a core material having a cylindrical shape coated with a conductive layer having an electric resistance that varies in a longitudinal direction of the cylindrical shape upon contact with a low molecular weight organic liquid, wherein the conductive layer is made of a substantially non-crosslinked material having a Shore A hardness of not more than 70 which is mainly composed of thermoplastic elastomer and conductive carbon.

2. A low molecular weight organic liquid detection sensor according to claim 1, wherein the core material is formed by providing an electrical insulating coating on a wire conductor.

3. A low molecular weight organic liquid detection sensor according to claim 2, wherein the wire conductor and the conductive layer are electrically connected at one end of the sensor, and the wire conductor and the conductive layer respectively have electrical connections for connecting to an electric resistance measurement instrument at another end of the sensor.

4. A low molecular weight organic liquid detection sensor according to claim 3, wherein the electrical connections are provided with a watertight insulation coating.

5. A low molecular weight organic liquid detection sensor according to claim 1, wherein electrodes for electric resistance measurement are respectively mounted on the both ends of the conductive layer of the wire body.

6. A low molecular weight organic liquid detection sensor according to claim 1, which is housed in an electrical insulating porous body.

7. A low molecular weight organic liquid detection sensor according to claim 1, wherein the initial electric resistance of the conductive layer is set to not more than 500 kΩ.

8. A low molecular weight organic liquid detection sensor according to claim 1, including means for measuring electrical resistance of the conductive layer in the longitudinal direction of the cylindrical shape.

9. A low molecular weight organic liquid detector comprising:
- a low molecular weight organic liquid detection wire-form sensor formed by coating a core material with a conductive layer made of a substantially non-crosslinked material having a Shore A hardness of not more than 70 which is mainly composed of thermoplastic elastomer and conductive carbon;
- a means electrically connected to the sensor for detecting electric resistance variation; and
- a means for transmitting the detected variation in the electric resistance as an alarm signal.

10. A low molecular weight organic liquid detector according to claim 9, wherein electrical connections are provided with a watertight insulation coating.

11. A low molecular weight organic liquid detector according to claim 9, wherein the low molecular weight organic liquid detection sensor is housed in an electrical insulating porous body.

12. A low molecular weight liquid detector according to claim 9, including means for detecting water connected to the sensor.

13. A low molecular weight organic liquid detector according to claim 12, wherein the means for detecting water is contained in an electrical insulating porous body.

14. A low molecular weight organic liquid detector according to claim 13, wherein the electrical insulating porous body is a braid body, and the means for detecting water is braided into said braid body.

15. A low molecular weight organic liquid detector according to claim 13, wherein the means for detecting water braided into the braid body is formed so that at least one yarn from each of a weft group and a warf group are copper wires coated with one of a water soluble polymer, a water absorbable polymer and a water swellable polymer.

16. A low molecular weight organic liquid detector according to claim 9, wherein an initial electric resistance of the low molecular weight organic liquid detection wire-form sensor is set to not more than 500 kΩ.

17. A low molecular weight organic liquid detection sensor in a wire form, which comprises a core material of a wire conductor having an electrically insulating layer formed thereon, the core material having a conductive layer thereon, the conductive layer having an electric resistance that varies upon contact with a low molecular weight organic liquid and being mainly composed of a thermoplastic elastomer and a conductive carbon, and the initial electric resistance of the conductive layer being set to not more than 500 kΩ, wherein the wire conductor and the conductive layer are electrically connected at one end of the sensor, and the wire conductor and the conductive layer are respectively connected to a lead wire which is connected to an instrument for measuring electrical resistance at another end of said sensor.

18. A low molecular weight organic liquid detection sensor in a wire form according to claim 17, which is loosely housed in an electrical insulating porous body.

19. A low molecular weight organic liquid detector comprising:
- a low molecular weight organic liquid detection sensor in a wire form;
- an electrically insulating porous body loosely housing the sensor;
- a means electrically connected to said sensor for detecting an electric resistance variation; and
- a means for transmitting the detected variation in electric resistance as an alarm signal,
- wherein the detection sensor comprises a core material of a wire conductor having an electrically insulating layer formed thereon, the core having a conductive layer thereon, the conductive layer having an electric resistance that varies upon contact with a low molecular weight organic liquid and being mainly composed of a thermoplastic elastomer and a conductive carbon, the initial electric resistance of the conductive layer being set to not more than 500 kΩ, the wire conductor and the conductive layer being electrically connected at one end of the sensor, the wire conductor and the conductive layer being respectively connected to a lead wire which is connected to a measurement instrument at another end of the sensor.

* * * * *